(12) United States Patent
Granger et al.

(10) Patent No.: US 6,436,416 B2
(45) Date of Patent: Aug. 20, 2002

(54) COSMETIC SKIN CONDITIONING COMPOSITIONS CONTAINING HIGH PERFORMING RETINYL ESTERS

(75) Inventors: Stewart Paton Granger, Sharnbrook Bedford (GB); Susanne Teklits Iobst, Maywood, NJ (US); Marieann Barratt, Oak Ridge, NJ (US); Richard John Kosturko, Nutley, NJ (US); Victor DeFlorio, Cranford, NJ (US); Ian Richard Scott, Allendale, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/837,063

(22) Filed: Apr. 18, 2001

Related U.S. Application Data

(60) Provisional application No. 60/198,030, filed on Apr. 18, 2000.

(51) Int. Cl.$^7$ .............................. A61K 7/00; A61K 7/40; A61K 7/48; A61K 31/21; A61K 31/215
(52) U.S. Cl. ...................... 424/401; 424/70.1; 424/420; 424/59; 514/506; 514/828; 514/847; 514/844; 514/557; 514/529
(58) Field of Search ................. 424/401, 70.1, 424/420, 59; 514/159, 529, 557, 844, 847, 506, 828

(56) References Cited

U.S. PATENT DOCUMENTS

| | | | |
|---|---|---|---|
| 4,992,265 A | | 2/1991 | Davis et al. .................. 424/70 |
| 5,037,850 A | | 8/1991 | Elliot et al. .................. 514/529 |
| 5,196,410 A | * | 3/1993 | Francoeur et al. ........... 514/159 |
| 5,605,933 A | | 2/1997 | Duffy et al. .................. 514/557 |
| 5,723,139 A | | 3/1998 | Granger ....................... 424/401 |
| 5,885,595 A | | 3/1999 | Corey et al. ................. 424/401 |
| 6,042,841 A | * | 3/2000 | Alaluf et al. ................. 424/401 |
| 6,136,985 A | * | 10/2000 | Millis .......................... 424/59 |

FOREIGN PATENT DOCUMENTS

| | | |
|---|---|---|
| EP | 512 814 | 11/1992 |
| EP | 0 709 084 A | 5/1996 |
| EP | 710 478 | 5/1996 |
| EP | 0 807 429 A | 11/1997 |
| WO | 94/09756 | 5/1994 |
| WO | 99/32105 | 7/1999 |

OTHER PUBLICATIONS

V. Azaias–Braesco, A. Forget, M. Mercier, and P. Grolier; *Rapid Synthesis and Purification of Vitamin A Esters, Nutrition and Food Safety Laboratory*, JAOCS, vol. 69, No. 12 (Dec. 1992).

International Search Report PCT/EP 01/03835 dated Sep. 25, 2001.

\* cited by examiner

*Primary Examiner*—Frederick Krass
*Assistant Examiner*—Clinton Ostrup
(74) *Attorney, Agent, or Firm*—Ellen Plotkin

(57) ABSTRACT

Cosmetic skin care compositions containing a high performing retinyl ester which is an ester of retinol with $C_{18}$, unsaturated, non-essential, cis-6 and/or cis-12 fatty acid. The ester is preferably selected from the group consisting of gamma-retinyl linolenate, retinyl petroselinate, and retinyl cis-12-octadecenoate.

6 Claims, No Drawings

COSMETIC SKIN CONDITIONING COMPOSITIONS CONTAINING HIGH PERFORMING RETINYL ESTERS

This Application claims the benefit under 35U.S.C. §119 (R) of U.S. provisional Application No. 60/198,030 filed Apr. 18, 2000.

FIELD OF THE INVENTION

Cosmetic methods and compositions for conditioning human skin by topical application to the skin of cosmetic compositions containing selected retinyl esters.

BACKGROUND OF THE INVENTION

Cosmetic products which improve the appearance of skin are increasingly popular with consumers. These products aim to alleviate or delay the signs of aged or photoaged skin, such as fine lines and wrinkles, dry and sagging skin. Although the marketplace offers a variety of products, cosmetic manufacturers continue the quest for alternative actives, in order to provide a consumer with a choice of products.

A number of retinyl esters are disclosed in prior art. See for example U.S. Pat. No. 5,723,139; U.S. Pat. No. 5,885,595; WO 94/09756; EP 0 512 814; U.S. Pat. No. 5,723,139; EP 0710 478; U.S. Pat. No. 5,037,850; U.S. Pat. No. 4,992,265; U.S. Pat. No. 5,605,933.

The art cited above does not disclose cosmetic compositions containing retinyl esters included in the present invention.

SUMMARY OF THE INVENTION

The present invention includes a skin conditioning composition comprising:
 (a) from 0.0001% to 10% wt. % of a a retinyl ester which is an ester of retinol with $C_{18}$, unsaturated, non-essential, cis-6 and/or cis-12 fatty acid;
 (b) a cosmetically acceptable vehicle.

The present invention also includes a cosmetic method of improving or preventing the condition of wrinkled, lined, dry, flaky, aged or photodamaged skin and improving skin thickness, elasticity, flexibility, radiance, glow and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to normal healthy skin to prevent or reduce the deteriorative changes.

The following detailed description and the examples illustrate some of the effects of the inventive compositions. The invention and the claims, however, are broader than the problems solved and are not limited thereto.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, legs, hands and scalp.

For the avoidance of doubt the word "comprising" is intended to mean "including" but not necessarily "consisting of" or "composed of". In other words, the listed steps or options need not be exhaustive.

The retinyl esters included in the present invention area collectively termed herein as "high performing retinyl esters" or "HPRE". The HPRE included in the present invention are selected to optimize the beneficial effects on skin. It has been found that esters of C18 fatty acids perform better than retinyl palmitate (a C16 retinyl ester extensively used in commercial cosmetic compositions). According to the present invention, retinyl esters should preferably hydrolyze on the skin and the products of the hydrolysis (retinol and a fatty acid) penetrate into the skin, to provide benefits of retinol and the fatty acid. Hence, the present invention includes esters of unsaturated fatty acids, molecules that are liquid at body temperature and thus can penetrate more easily into the layers of the skin than saturated fatty acids, which are solids at body temperature. The HPRE are esters of non-essential fatty acids, to maximize their availabilty to skin cells (i.e. minimizing the biological competion that arises from the supplementation of essential fatty acids). The cis-6 and or cis-12 acids are selected to maximize the beneficial effect on the skin, while avoiding the potential irritating retinol effect on the skin (the cis-6 and/or cis-12 fatty acids tend to have an anti-irritant activity).

The preferred retinyl ester suitable for the inclusion in the inventive composition is selected from the group consisting of gamma-retinyl linolenate, retinyl petroselinate and retinyl cis-12-octadecenoate. The HPRE are included in the inventive compositions in an amount of 0.0001% to 10%, preferably from 0.01% to 1% more preferably from 0.01% to 0.5% and most preferably from 0.05% to 0.3%. The HPRE maybe prepared by methods well known for making esters of retinyl and as described in example 1. The most preferred HPRE to be included in the inventive compositions is retinyl petroselinate as it offers the benefit of the other HPRE at lower cost. The preferred HPRE included in the present invention have the following structures:

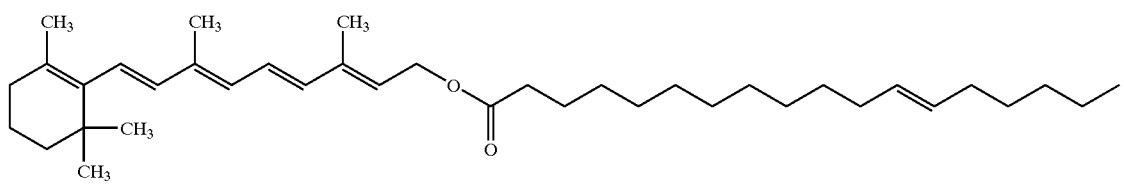

cis-12-Retinyl Octadecenoate (MW = 550)

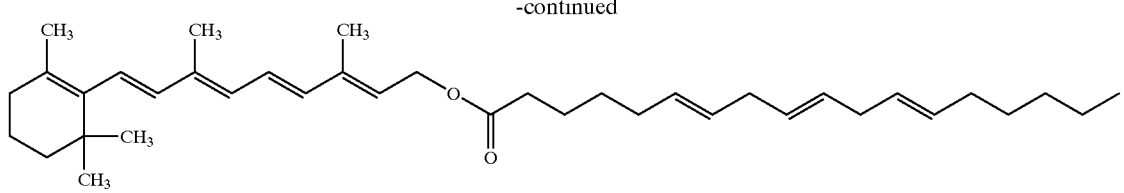

cis-6,9,12-Retinyl Octadecatrienoate (MW = 546)

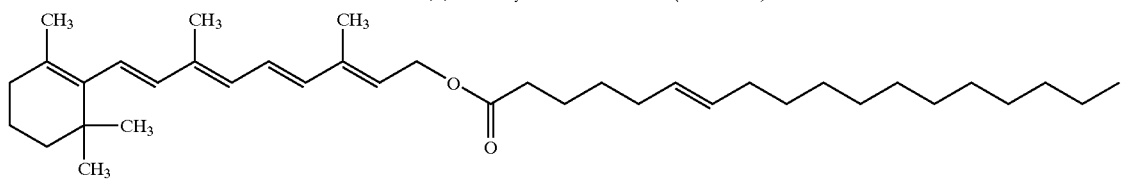

Retinyl Petroselinate (MW = 550)

Cosmetically Acceptable Vehicle

The composition according to the invention also comprises a cosmetically acceptable vehicle to act as a dilutant, dispersant or carrier for the HPRE in the composition, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 $mm^2/s$ (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, the amount of water is at least 50 wt. % of the inventive composition, most preferably from 60 to 80 wt. %, by weight of the composition. The preferred compositions are oil-in-water emulsions, containing at least 60%, preferably at least 80% water.

Optional Skin Benefit Materials and Cosmetic Adjuncts

The inventive compositions preferably include sunscreens to further lower skin's exposure to harmful UV rays.

Sunscreens include those materials commonly employed to block ultraviolet light. Illustrative compounds are the derivatives of PABA, cinnamate and derivatives of salicylate. For example, octyl methoxycinnamate and 2-hydroxy4-methoxy benzophenone (also known as oxybenzone) can be used. Octyl methoxycinnamate and 2-hydroxy4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include trisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicon-based anhydrous composition within a gelatne capsule), incorporated by reference herein. The invention accordingly also provides a closed container containing a cosmetically acceptable composition as herein defined.

The following specific examples further illustrate the invention, but the invention is not limited thereto.

EXAMPLE 1

This example illustrates synthesis of the HPRE included in the inventive compositions.

General Procedure for Synthesis of Retinyl Esters

Into a clean, dry three necked ambered flask charge 1.0 equivalents of retinol, 1.0 equivalents of fatty acid and 100 mls of hexane. Equip flask with a stir bar, thermometer, addition funnel and nitrogen bubbler. Cool contents of the flask to ~5° C. under a nitrogen blanket before adding 0.01 equivalents of 4-dimethylaminopyridine. Warm the reaction mixture to 10–15° C. before adding a solution of 1.0 equivalents of dicyclohexylcarbodiimide in 15–20 mls of hexane dropwise through the addition funnel over thirty minutes. After the addition is complete, stir the reaction at 15–20° C. for four hours.

Cool the reaction mixture to 5–10 C. before filtering under vacuum to remove the dicyclohexylurea byproduct. Extract the filtrate with water, once with sodium bicarbonate solution, again with water, once with 0.1 N hydrochloric acid solution and three times with water. Isolate the organic layer, dry over magnesium sulfate, filter and concentrate.

Synthesis of Retinyl Petroselinate

Into a clean, dry three necked ambered flask were charged 2.0 g (7.1 mmoles) of retinol, 2.0 g (7.1 mmoles) of petroselinic acid and 100 mls of hexane. The flask was equipped with a stir bar, thermometer and addition funnel. The contents of the flask were cooled to ~5° C., before 8 mg (0.07 mmoles) of 4-dimethylaminopyridine were added. The reaction mixture was warmed to 10–15° C. before a solution of 1.4 g (7.1 moles) of dicyclohexylcarbodiimide, in 15–20 mls of hexane, were added slowly through the addition funnel over thirty minutes. After the addition was complete, the reaction stirred at 15–20° C. for four hours.

The reaction mixture was cooled to 5–10° C. before being filtered under vacuum to remove the dicyclohexylurea byproduct. The filtrate was extracted with water, once with sodium bicarbonate solution, again with water, once with 0.1 N hydrochloric acid solution and three times with water. The organic layer was isolated, dried over magnesium sulfate, filtered and concentrated to give 2.3 g of a viscous orange oil. The crude product was purified on a silica gel column using 95/5 hexane/ether as the mobile phase.

$^1$H NMR (200 MHz, CDCl$_3$ with TMS) ppm: —CH$_2$CO$_2$— (4.7, d, 2H) IR: 1753 cm$^{-1}$ (carbonyl ester)

Synthesis of Retinyl-cis-6,9,12-Octadecatrienoate (Gamma Linolenate)

The ester was synthesized using the above general procedure with 3.0 g of cis-6,9,12-octadecatrienoic acid (gamma linolenic). 4.5 of orange oil were recovered prior to purification by silica gel chromatography.

$^1$H NMR (200 MHz, CDCl$_3$ with TMS) ppm: —CH$_2$CO$_2$— (4.7, d, 2H) IR: 1740 cm$^{-1}$ (carbonyl ester)

Synthesis of Retinyl-cis12-Octadecenoate

The ester was synthesized using the above general procedure with 1.0 g of cis-12-octadecenoic acid.

1.3 g of orange oil were recovered prior to purification by silica gel chromatography.

$^1$H NMR (200 MHz, CDCl$_3$ with TMS) ppm: —CH$_2$CO$_2$— (4.6, d, 2H) IR: 1746 cm$^{-1}$ (carbonyl ester)

EXAMPLE 2

The activity of various retinyl esters was tested in Procollagen I assay and CRABP-2 assay.

Procollagen I assay:

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. lnv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Seed passage 3 (P3) fibroblasts in 6-well tissue culture treated dishes at a density of ~10,000 cells/well.

Culture cells until ~70% confluent in high glucose Dulbecco's Modified Eagles Medium (DMEM).

When cells are ~70% confluent, replace with fresh medium, dose with actives and continue culturing until cells are 100% confluent.

Remove media and store at 4° C.

Dilute 20 µl conditioned (treated) media in 200 µl unconditioned DMEM.

Soak nitrocellulose membrane and 3 sheets of filter paper in 1×TBS (tris buffered saline, pH=7.3).

Set up Bio-Rad slot blot apparatus with filter paper on bottom, nitrocellulose membrane on top. Add 100 µl TBS/well. Vacuum dry.

Remove membrane from apparatus and place in blocking solution (5% milk powder in phosphate buffered saline (PBS)) for 1 hr at room temperature or overnight at 4° C.

Primary antibody-Remove membrane from blocking solution and incubate for 1.5 hours at room temperature or overnight at 4° C. with 1.5 ml rat anti-human procollagen amino-terminal antibody (Chemicon MAB1912) 1:100 in TBS with 0.1% bovine serum albumin (BSA).

Remove membrane, was 3×(10 minutes/wash) in TBS/0.1% tween 20.

Secondary antibody-incubate for 1 hour at room temperature or overnight at 4° C. in 2 ml 1:1000 biotinylated anti-rat peroxidase conjugated antibody (Vector Labs).

Remove membrane from secondary antibody and was 3×(10 minutes/wash) in TBS/0.1% tween 20.

Preincubate 3 ml PBS with 30 μl each of solutions A and B from Vectastain kit for 30 minutes.

Place membrane in biotin/avidin solution (A and B from above) for 30 minutes in a sealed plastic bag on an orbital shaker.

Wash twice (15 minutes each wash) in TBS/0.1% Tween 20.

Stain membrane using AEC solution (12.5 mg 3-amino 9-ethyl carbazole, 3.125 ml dimethyl formamide, 21.5 ml 0.2M NaOAc buffer (23 ml acetic acid/qs to 2 liters with deionozed water-adjust pH to 5.2 with NaOH) and 12.5 μl $H_2O_2$.)

Stain until color develops. Stop reaction by rinsing with tap water.

Scan using a laser densitometer and quantified as % over control (with control at 100%).

CRABP-2 assay:

Within the cells, retinol and retinoic acid are bound to specific cellular binding proteins. Two of the major proteins are CRABP-1 and CRABP-2 (Roos et al., Pharmacological reviews: 50, 315–333, 1998). These proteins regulate the intracellular concentration of retinoids by acting as either storage or shuttle proteins in retinoid metabolism. The levels of CRABP protein are regulated by the amount of retinoic acid within the cells. Higher cellular levels of retinoids increase the expression of CRABP-2. Therefore, the amount of this protein in the cells is a measure of the retinoid activity of the cells. Skin cells contain high levels of CRABP-2 both in the epidermis and the dermis. CRABP-2 response to retinoid administration in is used as a reproducible measure of retinoid bioactivity that predict human skin responses (Elder et al., J. Invest. Dermatol., 106: 517–521, 1996). Increase in CRABP-2 is also associated with increased epidermal differentiation, and dermal retinoid action. Therefore, in these studies we used CRABP-2 expression of pig skin epidermis as a measure of retinoid activity leading to increased epidermal differentiation (skin conditioning and dry skin benefit) and dermal collagen and extracellular matrix synthesis (antiaging, anti wrinkling benefits).

Pig skin was received, scrubbed with Vionex detergent, and dermatomed at a thickness of 0.058 cm and allowed to wash in preliminary medium on a shaker for an hour with three solution changes.

7 mm punches were taken and allowed to sit in final medium overnight. The next day, the medium was refreshed with final medium 1 mL per well. One day later, the plates received fresh final medium,and topically dosed with 5 μl of the active(s) in an ethanol vehicle.

After four days, the biopsies will be removed from the plates, washed with PBS in a concial tube, and frozen at −80° C. for future use.

After thawing, the epidermis was separated and boiled in urea and sample buffer, after which protein quantitation was possible.

16% 15 lane acrylamide gels were loaded ewith the appropriate samples and run until all the proteins were separated based upon their molecular weight.

The gels were transferred onto PVDF membranes at 25 constant Volts for 2.5 hours.

The membranes were blocked with 5% milk in TBST (Tween 0.05%) for one hour at room temperature.

Primary Ab exposure 1:1,000 in 1% milk TBS soln for one hour, followed by six washes with TBST over a period of one hour.

Secondary antibody exposure (anti-mouse—AP) at a dilution of 1:2,000 in 1% milk TBS one hour at room temp on shaker, followed by six washes with TBST over a period of one hour.

The membrane was drip-dried, and placed protein side up on a heat-sealable bag. The chemiluminescent reagent was applied and incubated at room temp for 5 minutes.

The bag was then heat sealed and incubated at 37° C. for 15 minutes, after which the membrane was exposed to x-ray film for band resolution.

The bands in the film were quantified by densitometric scanning, the data from triplicate samples were calculated as % of control and expressed in the following tables as % increase over control (with control as 100%).

The results that were obtained are summarized in Tables 1 and 2.

TABLE 1

| Procollagen assay | | | |
|---|---|---|---|
| Compound | Concentration | % over control | p over control |
| Experiment 1 | | | |
| Gamma-retinyl linolenate | $10^{-5}$ M | 225 | **p<0.05 |
| Retinyl petroselinate | $10^{-6}$ M | 110 | **p<0.05 |
| Experiment 2 | $10^{-6}$ M | 28 | **p<0.05 |
| Retinyl cis-12-Octadecenoate | | | |
| Experiment 3 | $10^{-7}$ M | 24 | (not significant) |
| Retinyl Palmitate | | | |

TABLE 2

| CRABP-2 assay | | | |
|---|---|---|---|
| Compound | Concentration | % over control | p over control |
| Gamma-retinyl linolenate | $10^{-4}$ M | 882 | **p < 0.05 |
| Retinyl Petroselinate | $10^{-3}$ M | 522 | **p < 0.05 |
| Retinyl cis-12-Octadecenoate | $10^{-4}$ M | 993 | **p < 0.05 |
| Retinyl Palmitate | $10^{-3}$ M | 444 | (not significant) |

It can be seen from Tables 1 and 2 that HPRE included in the present invention were more efficacious in both assays than retinyl palmitate.

EXAMPLE 3

Example 3 illustrates topical compositions according to the present invention. The compositions can be processed in conventional manner. They are suitable for cosmetic use. In particular the compositions are suitable for application to wrinkled, rough, flaky, aged and/or UV-damaged skin and/or oily skin to improve the appearance and the feel thereof as well as for application to healthy skin to prevent or retard deterioration thereof.

| INGREDIENT | % w/w |
|---|---|
| OIL-IN-WATER EMULSION | |
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Retinyl petroselinate | 8.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| OIL-IN-WATER EMULSION | |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Gamma-retinyl linoleate | 8.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total → | 100.00 |
| WATER-IN-OIL EMULSION | |
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| cis-12-octadecenoate | 5.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| HYDRO-GEL | |
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |

| INGREDIENT | % w/w |
|---|---|
| retinyl petroselinate | 1.00 |
| Methylparaben | 0.30 |
| Polysorbate 20 | 0.25 |
| Disodium EDTA | 0.10 |
| Germall II | 0.10 |
| Total → | 100.00 |
| ANHYDROUS SERUM | |
| Cyclomethicone | 72.40 |
| Gamma-retinyl linoleate | 5.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total → | 100.00 |
| HYDRO-ALCOHOLIC GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Cis-12-octadecendate | 1.00 |
| Methylparaben | 0.30 |
| Polysorbate 20 | 0.25 |
| Disodium EDTA | 0.10 |
| Germall II | 0.10 |
| Total → | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising:
   (a) from about 0.0001% to about 10% by weight of said composition of a retinyl ester which is an ester of retinol with $C_{18}$ unsaturated, non-essential, cis-6 and/or cis-12 fatty acid selected from the group consisting of cis-6,9,12-Retinyl Octadecetrienoate and retinyl cis-12-octadecenoate; and
   (b) a cosmetically acceptable vehicle.

2. The composition of claim 1, wherein the ester is cis-6,9,12-Retinyl Octadecetrienoate.

3. The composition of claim 1 wherein the ester is retinyl cis-12-octadecenoate.

4. A cosmetic method of improving the appearance of wrinkled, lined, dry, flaky, aged or photodamaged skin and improving skin thickness, elasticity, flexibility and plumpness, the method comprising applying to the skin the composition of claim 1.

5. A cosmetic method of increasing procollagen I production by fibroblasts, the method comprising applying to the skin the composition of claim 1.

6. A cosmetic method of increasing CRABP-2 level in epidermis, the method comprising applying to the skin the composition of claim 1.

* * * * *